US00PP23616P3

(12) United States Plant Patent
Blom

(10) Patent No.: US PP23,616 P3
(45) Date of Patent: May 21, 2013

(54) ***CHRYSANTHEMUM* PLANT NAMED 'ZANMUDANDE'**

(50) Latin Name: ***Chrysanthemum×morifolium* Ramat.**
Varietal Denomination: Zanmudande

(75) Inventor: Wilhelmus Bernardus Blom, Leimuiden (NL)

(73) Assignee: Chrysanthemum Breeders Research Association B.V., Valkenburg Z-H (NL)

( * ) Notice: Subject to any disclaimer, the term of this patent is extended or adjusted under 35 U.S.C. 154(b) by 94 days.

(21) Appl. No.: 13/200,327

(22) Filed: Sep. 23, 2011

(65) Prior Publication Data
US 2013/0081163 P1 Mar. 28, 2013

(51) Int. Cl.
*A01H 5/00* (2006.01)

(52) U.S. Cl.
USPC ..... Plt./295

(58) Field of Classification Search ..... Plt./295
See application file for complete search history.

*Primary Examiner* — Annette Para
(74) *Attorney, Agent, or Firm* — Steptoe & Johnson LLP

(57) ABSTRACT

A *chrysanthemum* plant named 'Zanmudande' characterized by its medium sized blooms with yellow ray florets and prolific branching; natural season flower August 13 (week 33) blooming for a period of 5 weeks.

3 Drawing Sheets

Botanical designation: *Chrysanthemum×morifolium* Ramat.

Cultivar denomination: 'Zanmudande'.

RELATED CULTIVARS

This new plant cultivar 'Zanmudande' is related to 'Zanmutang' (U.S. Plant patent application Ser. No. 13/200,328), a sibling from the same cross with parent plants.

BACKGROUND OF THE INVENTION

The present invention relates to a new and distinct cultivar of *Chrysanthemum* plant, botanically known as *Chrysanthemum×morifolium* Ramat., commercially known as a garden mum, and hereinafter referred to by the cultivar denomination 'Zanmudande'. 'Zanmudande' is a product of a breeding and selection program for outdoor pot mums (garden mums) which had the objective of creating new cultivars with a double type inflorescence, a natural season flower date around August 13 (week 33), blooming for a period of 5 weeks. 'Zanmudande' is a seedling resulting from a cross of the female parent id 21570 with the male parent id 23262. Both parents are unpatented plants. Plants of the new cultivar 'Zanmudande' differ from plants of the female parent in the following characteristics. (1) Plant vigor and (2) Natural season flower date. (1). Plants of the seedling are more vigorous than plants of the female parent. (2) Plants of the seedling flower earlier in the season than plants of the female parent. Whileas plants of the new cultivar 'Zanmudande' differ from plants of the male parent in the following characteristics. (1) Plant vigour and (2) Natural season flower date. (1). Plants of the seedling are less vigorous than plants of the male parent. (2) Plants of the seedling flower earlier in the season than plants of the male parent.

The new and distinct cultivar was discovered and selected as a flowering plant by Wilhelmus Bemardus Blom on a cultivated field in Rijsenhout, The Netherlands in 2005. The first act of asexual production of 'Zanmudande' was accomplished when vegetative cuttings from the initial selection in 2005 were propagated further in a controlled environment in Rijsenhout, The Netherlands. The new cultivar has been found to retain its distinctive characteristics through successive propagations.

BRIEF DESCRIPTION OF THE DRAWINGS

The present invention of a new and distinct variety of *Chrysanthemum* is shown in the accompanying drawings, the color being as nearly true as possible with color photographs of this type.

DESCRIPTION OF THE INVENTION

Figure 1:
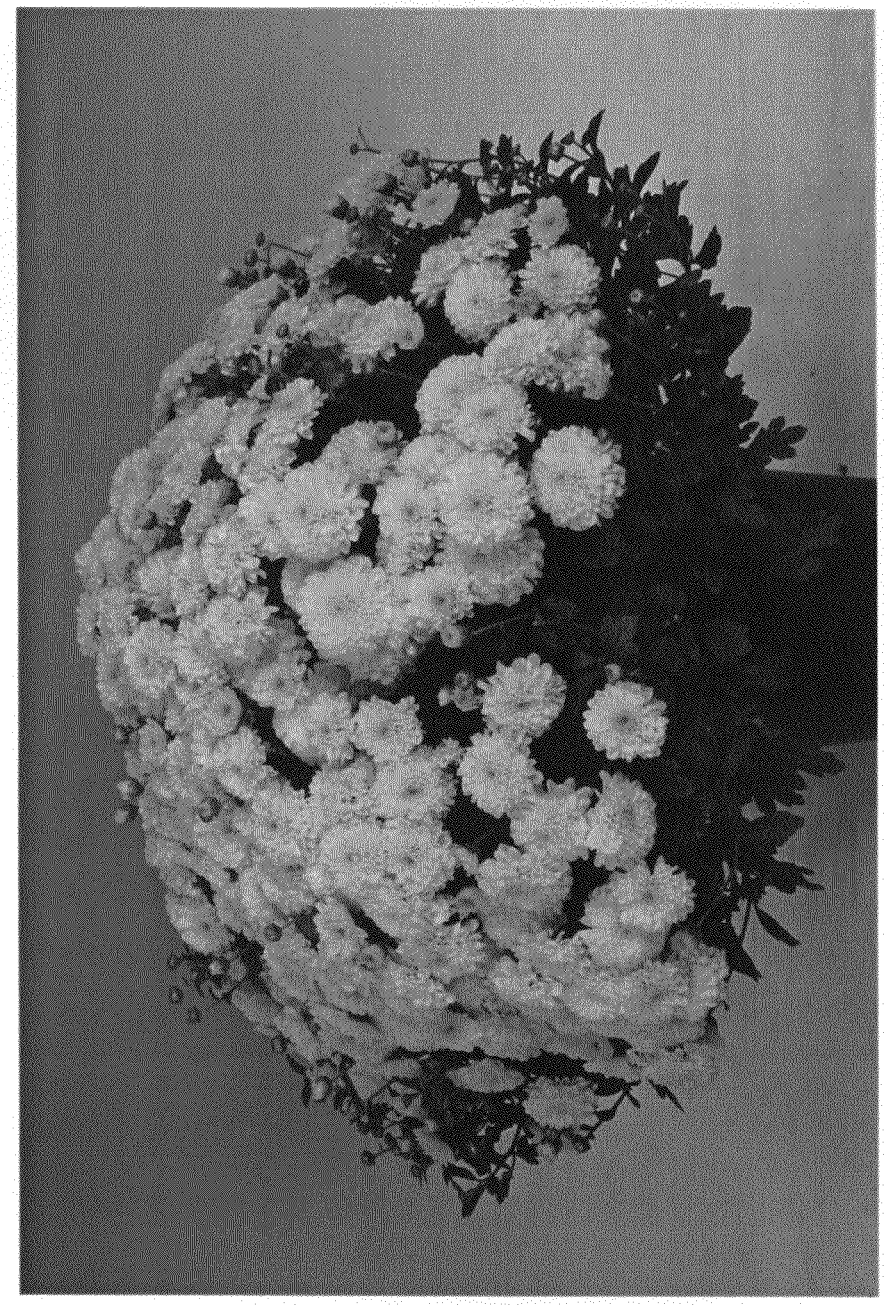
FIG. 1 shows a plant of the cultivar in full bloom.
Figure 2:
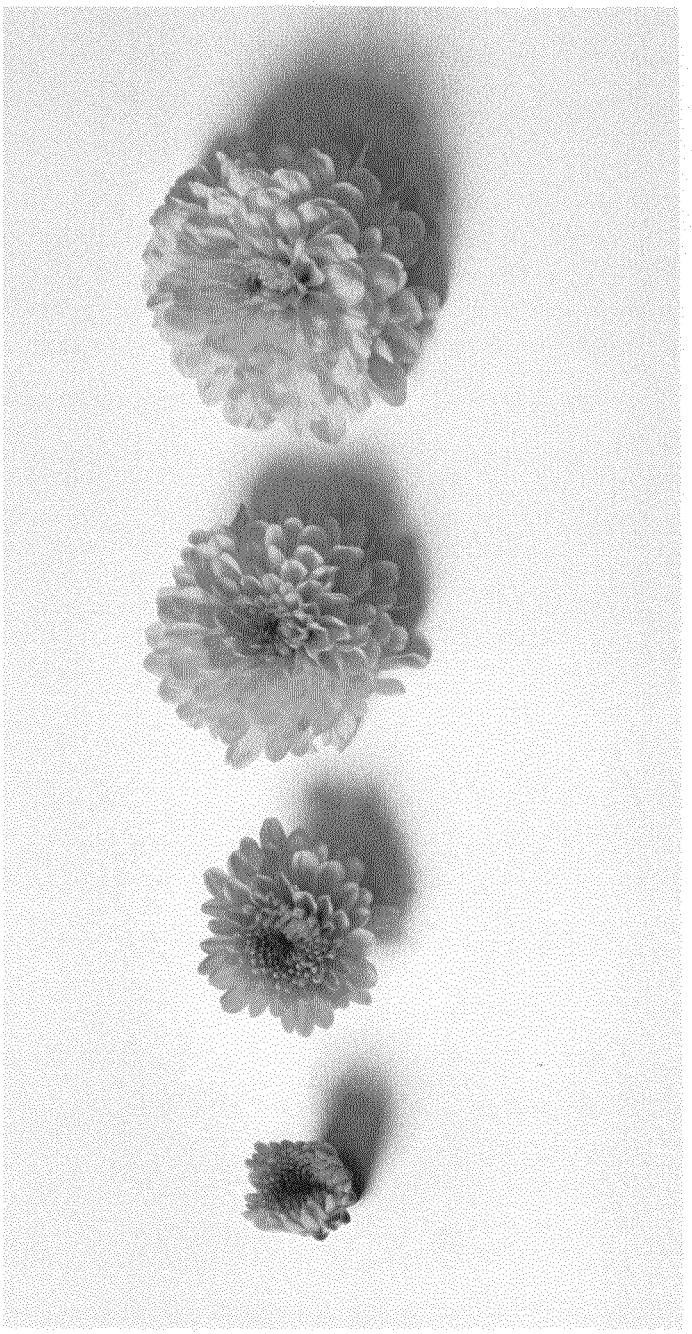
FIG. 2 shows the various stages of bloom of the new cultivar.
Figure 3:
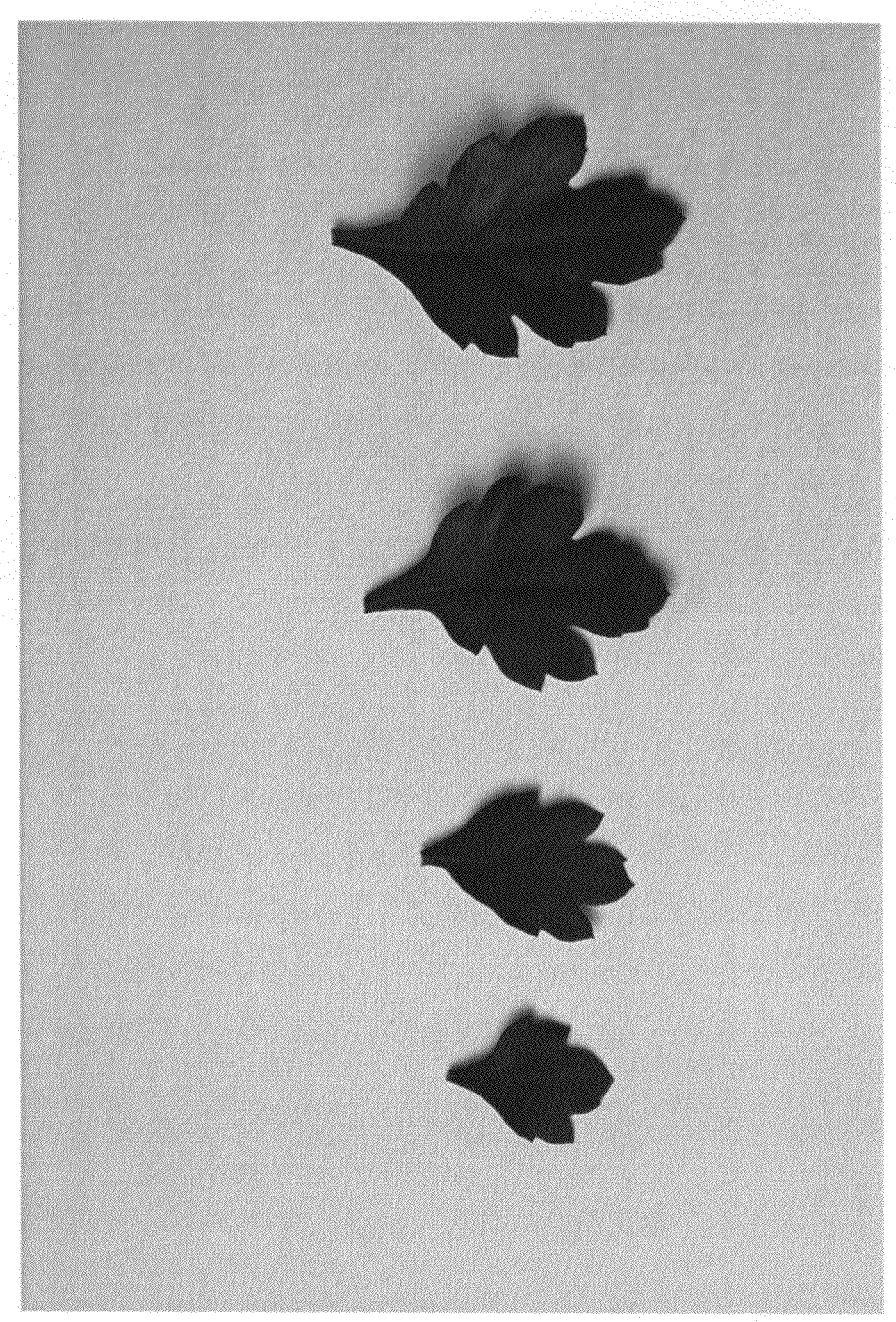
FIG. 3 shows the various stages of foliage of the new cultivar.

The observations and measurements were gathered from plants grown out door in Rijsenhout, The Netherlands under natural day length and temperature and planted in week 23 in 2005. The natural blooming date of this crop was August 13 (week 33). The average height of the plants was 35 cm. No growth retardants were used. No tests were done on disease or insect resistance or susceptibility. No tests were done on cold or drought tolerance. This new variety produces medium sized blooms with yellow ray florets blooming for a period of 5 weeks.

From the cultivars known to inventor the most similar existing cultivar in comparison to 'Zanmudande' are 'Mermaid Yellow Improved' (U.S. Plant Pat. No. 18,905) and 'Zanmugolmine' (U.S. Plant Pat. No. 22,618). When the three cultivars are being compared the following differences are noticed: (1) Inflorescence size. And (2) Color ray-florets. (1) The inflorescences of 'Mermaid Yellow' are larger than those of 'Zanmudande' and 'Zanmugolmine'. (2) The ray florets are more dark yellow in 'Zanmudande' than in 'Mermaid Yellow' and 'Zanmugolmine'.

The following is a description of the plant and characteristics that distinguish 'Zanmudande' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, edition 2001.

TABLE 1

| Detailed Botanical Description | |
|---|---|
| **Bud** | |
| Size | Small; cross-section 6 mm, height 6 mm |
| Shape | Round |
| Texture | Pubescent |
| Outside Color | Greyed-green 138A |
| **Phyllaries** | |
| Number | 18-20, arranged in 2 rows |
| Shape | Elliptic |
| Apex | Acute |
| Base | Truncate |
| Margin | Entire |
| Color | Upper surface: Green 137B<br>Lower surface: Green 137D |
| Length and width | 5 mm; 3 mm |
| Texture | Pubescent |
| **Inflorescences** | |
| Type | Double |
| Height | 1.8-2 cm |
| Diameter | 5 cm |
| Peduncle length | 8-9 cm |
| Peduncle color | Green 137D |
| Peduncle diameter | 1.5 mm |
| Peduncle texture | Pubescent |
| Number per branch | Approx 5 inflorescences |
| Duration of flowering | 5 weeks |
| Seeds | Produced in small quantities, ovate, Greyed-brown 199A, length 1.5 mm, diameter 0.5 mm |
| Fragrance | Faint chrysanthemum odor |
| **Color** | |
| Center of inflorescences | Immature stage: Yellow-orange 15A<br>Mature stage: Yellow 13 A |
| Color of upper surface of the ray-florets | Yellow 12B |
| Color of the lower surface of the ray-florets | Yellow 11B |
| Tonality from Distance | A garden mum with yellow blooms |
| Color of the ray-florets after aging of the plant | Yellow 12C |
| **Ray florets** | |
| Texture | Upper and lower surface smooth |
| Number | 150-170 |
| Shape | Elliptic |
| Apex | Dentate |
| Base | Attenuate |
| Cross-section | Concave |
| Longitudinal axis of majority | Straight to Reflexing |
| Length of corolla tube | 3 mm |
| Ray-floret margin | Entire |
| Ray-floret length | 1.2-2 cm |
| Ray-floret width | 6-8 mm |
| Ratio length/width | Medium |
| Disc florets | Absent |

TABLE 1-continued

| Detailed Botanical Description | |
|---|---|
| **Receptacle** | |
| Color | Green 138D |
| Shape | Conical raised |
| Height | 3 mm |
| Diameter | 4 mm |
| **Reproductive Organs** | |
| Androecium | Absent |
| Gynoecium | Present on ray florets |
| Style color | Yellow-green 154C |
| Style Length | 3 mm |
| Stigma color | Yellow 7A |
| Stigma Width | 1 mm |
| Ovary | Enclosed in calyx |
| **Plant** | |
| Form | Grown as a spray type pot mum, outdoor raised and mounded |
| Growth habit | Spherical shape |
| Growth rate | High |
| Height | 35 cm |
| Width | 50 cm |
| Stem Color | Greyed-brown 199A |
| Stem Strength | Medium |
| Stem Brittleness | Brittle |
| Stem Anthocyanin Coloration | Not observed |
| Internode length | 3-4 cm |
| Length of lateral branch | From top to bottom 22 to 25 cm |
| Lateral branch color | Green 137 C |
| Lateral branch, attachment | Medium strength |
| Lateral branch diameter | 2 mm |
| Branching (average number of lateral branches) | Prolific with 7-8 breaks after pinching |
| Natural season blooming date | August 13 (week 33) |
| **Foliage** | |
| Leaf color | Upper side: Green 138A<br>Lower side: Green 138B |
| Color midvein | Upper side: Yellow-green 147D<br>Lower side: Yellow-green 148D |
| Size | Small; length 3.5-5 cm, width 2.4-3 cm |
| Quantity (number per lateral branch) | 20-22 |
| Shape | Elliptic |
| Texture upper side | Sparsely pubescent |
| Texture under side | Pubescent |
| Venation arrangement | Palmate |
| Shape of the margin | Serrated |
| Shape of Base of Sinus Between Lateral Lobes | Rounded |
| Margin of Sinus Between Lateral Lobes | Diverging |
| Shape of Base | Attenuate |
| Apex | Mucronulate |
| Petiole length | 0.6-1 cm |
| Petiole diameter | 2 mm |
| Petiole color | Yellow-green 147D |

TABLE 2

| Differences with the comparison varieties | | | |
|---|---|---|---|
| | 'Zanmudande' | 'Mermaid Yellow' | 'Zanmugolmine' |
| Inflorescence size | 5 cm | 5-7 cm | 5 cm |
| Color upper surface ray florets | Yellow 12B | Yellow 8B | Yellow 8A |

I claim:

1. A new and distinct *Chrysanthemum* plant named 'Zanmudande' as described and illustrated.

* * * * *